United States Patent
Krambeer et al.

(10) Patent No.: US 7,317,542 B2
(45) Date of Patent: Jan. 8, 2008

(54) METHOD AND DEVICE FOR OPTICALLY MEASURING THE SURFACE SHAPE AND FOR THE OPTICAL SURFACE INSPECTION OF MOVING STRIPS IN ROLLING AND PROCESSING INSTALLATIONS

(75) Inventors: Hagen Krambeer, Düsseldorf (DE); Ulrich Müller, Monheim (DE); Gustav Peuker, Mönchengladbach (DE); Harald Peters, Bergisch-Gladbach (DE); Detlef Sonnenschein, Essen (DE)

(73) Assignee: Betriebsforschungsinstitut VDEh-Institut für angewandte Forschung GmbH, Dusseldorf (DE)

( * ) Notice: Subject to any disclaimer, the term of this patent is extended or adjusted under 35 U.S.C. 154(b) by 62 days.

(21) Appl. No.: 10/503,665

(22) PCT Filed: Feb. 6, 2003

(86) PCT No.: PCT/EP03/01182

§ 371 (c)(1),
(2), (4) Date: Mar. 15, 2005

(87) PCT Pub. No.: WO03/067188

PCT Pub. Date: Aug. 14, 2003

(65) Prior Publication Data

US 2005/0157302 A1    Jul. 21, 2005

(30) Foreign Application Priority Data

Feb. 7, 2002    (DE) ............................... 102 05 132

(51) Int. Cl.
G01B 11/24    (2006.01)
(52) U.S. Cl. ........................ 356/603; 356/429; 356/604
(58) Field of Classification Search ..................... None
See application file for complete search history.

(56) References Cited

U.S. PATENT DOCUMENTS 4,165,939 A    8/1979    Woodrow et al.

(Continued)

FOREIGN PATENT DOCUMENTS

DE    197 09 992 C1    10/1998

(Continued)

OTHER PUBLICATIONS

International Preliminary Examination Report in International application No. PCT/EP03/001182.

(Continued)

Primary Examiner—Gregory J. Toatley, Jr.
Assistant Examiner—Juan D. Valentin, II
(74) Attorney, Agent, or Firm—Finnegan, Henderson, Farabow, Garrett & Dunner, LLP

(57) ABSTRACT

The invention relates to a method and a device for optically measuring the surface shape and for the optical surface inspection of moving elongated bodies, according to which surface shape measurement and surface inspection are integrated. A projector applies a line pattern to the object to be measured. A camera registers the surface of the object to be measured and compares the image information with a reference pattern. Two high-resolution cameras additionally detect surface defects on the object to be measured. The inventive measuring technique is especially suitable for a combined planarity and surface measurement of metal strips in rolling installations.

18 Claims, 6 Drawing Sheets

U.S. PATENT DOCUMENTS 4,349,277 A 9/1982 Mundy et al.
5,309,222 A 5/1994 Kamei et al.
5,367,378 A * 11/1994 Harding et al. ............. 356/613
5,488,478 A * 1/1996 Bullock et al. ............. 356/604
6,286,349 B1 9/2001 Müller et al.

FOREIGN PATENT DOCUMENTS

EP 0 063 761 A1 11/1982
WO WO 01/07352 A1 2/2001

OTHER PUBLICATIONS

John C. Badger, et al., "Automated Surface Inspection System", *Iron and Steel Engineer*, Mar. 1998, pp. 48-51.
International Search Report in PCT/EP03/01182 application.

* cited by examiner

METHOD AND DEVICE FOR OPTICALLY MEASURING THE SURFACE SHAPE AND FOR THE OPTICAL SURFACE INSPECTION OF MOVING STRIPS IN ROLLING AND PROCESSING INSTALLATIONS

CROSS-REFERENCE TO RELATED APPLICATIONS

This application is a national stage application under 35 U.S.C. § 371 of international application number PCT/EP03/01182, filed Feb. 6, 2003, which claims the benefit of priority from German application number 102 05 132.1, filed Feb. 7, 2002.

BACKGROUND OF THE INVENTION

1. Field of the Invention

The invention relates to a method and device for optically measuring the surface shape and for the optical surface inspection of moving strips in rolling and processing installations.

2. Description of Related Art

The contact measurement usually used in cold strip mills is only possible in the hot strip field at the expense of substantial outlay on maintenance, because of the high strip temperature of about 1000° C.

Strip flatness is therefor preferably measured without contact in hot rolling mills. For example, it is known to measure departures from flatness by means of spots of light projected on to the strip. The position in space of the light spot produced on the surface of the strip, preferably by means of a laser beam, is detected using a range finder.

The two plane position co-ordinates of a particular point on the surface are known from the position of the scanning or illuminating beam relative to the surface of the strip. The height co-ordinate of the point on the surface which is currently being measured is detected by a position sensitive sensor. The position of the image point on the sensor varies simultaneously with the height co-ordinate.

Using multiple sources of radiation and sensors a flatness image can be built up over the whole width of the strip which is made up from the results of measurement of the spots of light projected on the strip at particular distances apart. Nevertheless, in this method the regions between the points of light are not detected and in the case of continuous strip form strip-shaped measurement gaps in which the flatness is not determined. Moreover, this can result in measurement errors, for example through fluttering of the strip being detected by the measuring method as unevenness of the strip.

In the automobile industry it is known to measure relatively small surfaces using the moiré technique. In this method an interference pattern is produced on the surface of the object by means of a light source. The interference pattern is detected using a CCD (charge-coupled device) camera. The camera is arranged so that an angle is formed between the light source, the surface and the camera. By the use of a reference grid in the image plane a so-called moiré effect is obtained by superposition of the detected pattern and the reference pattern. The height differences can be determined quantitatively from the moiré lines.

The moiré technique provides more accurate measurement results than measurement using spots of light and moreover it covers substantially the whole of the surface to be measured and avoids the measurement gaps mentioned above. However, its use involves problems, particularly in a hot rolling mill.

To determine the height differences of the rolled strip a complicated conversion of the pattern detected by the camera is necessary. The height differences pictured as moiré lines cannot be converted into quantitative measured values in real time.

But in a rolling mill train rapid results are precisely what is required from measurements, since otherwise it is hardly possible to use the measurement for direct adjustment of the rolling parameters so as to improve the flatness of the continuous strip. Moreover for industrial application the fine interference patterns are lacking in contrast and intensity.

From U.S. Pat. No. 5,488,478 a device for surface measurement of a metal strip is known, which with the aid of laser beams creates lines on the metal surface, which are recorded by several linescan-cameras and are analysed for determining the surface geometry by comparison with reference patterns. This device necessitates a substantial constructional effort and moreover only allows for rough partial information about the surface geometry of the strip.

From DE 197 09 922 C1 a method is known, by which a line pattern is produced on the measurement surface, the line pattern is detected by a camera, which can resolve the line pattern, and the measurement data obtained are compared with a reference measurement. By means of a process control computer the measurement results are directly converted into control parameters for the finishing train and co-ordinated. This method especially has the advantage of a high insensitivity to disturbances, which are of importance in a rolling mill, since no sensitive laser optics are used, but an insensitive slide projector.

By measurement surfaces is to be understood here the surface of the strip-of a moving or stationary rolling stock.

A projector with a slide produces a line pattern on the strip surface. For this purpose the projector is mounted above the metal strip and projects the line pattern on the surface of the metal strip, so that the lines preferably run transverse to the strip surface and consequently record the whole width of the strip.

A CCD camera having a resolution of, for example, eight pixels per line detects the lines running transversely across the strip surface. In the event of absolute flatness of the strip a uniform pattern of straight lines with constant line spacing is formed.

Deviations of the strip surface from the ideal plane bring about a change in the spacing between the lines in the region of the unevenness. This change is recorded by the camera. It can be converted by calculation in a simple manner into differences in height by a comparison with an ideal pattern.

This system makes possible a rapid determination of the actual height differences of the strip surface and in this way permits measurement of continuous lengths of strip in real time. This has the advantage that the measurement results permit the rolling parameters to be adapted immediately after the appearance of unevenness.

This makes possible a measurement which is insensitive to spurious measurement results. Such spurious results are obtained with conventional measuring systems for example as a result of movement of the whole strip surface relative to the height co-ordinate (fluttering). Furthermore, the invention allows the transverse arching of the strip to be determined. Conventional measuring systems only measure the length of the strip fibres. In addition the intensity and thickness of the measurement lines can be adapted to meet different conditions. The problems of the fine, low-intensity and low-contrast moiré lines do not occur.

The system of the invention is particularly suitable for making a measurement on the strip emerging from the finishing stands combined with a measurement of the strip on the coiler. By this arrangement variations in the flatness of the strip due to cooling of the strip between the finishing stands and the coiler can be detected and evaluated for flatness control.

The measurement data can be evaluated for control of the finishing stands and of the coiler and for control of the coiling line.

Measurement results which incorporate a departure from an intended value bring about an immediate and interdependent adaptation of the parameters for the finishing stands, the cooling line and the coiler.

Besides its use for measurement of flatness in a finishing train the system in accordance with the invention can also be used in subsequent production lines, for example in the control of stretch straightening devices and in pickling lines.

In addition to the flatness the dimensional stability of the geometrical values, such as thickness, transverse thickness profile and width, aswell as the surface condition, which are detected by surface inspection systems, are part of the relevant quality characteristics in rolling and further processing of strips and sheet. Keeping tight tolerances is desirable and not only a measure for the quality of the products ready to sell, but also of importance for a course of the whole treatment process that is as free from disturbances as possible, especially with constantly increasing automation of the production processes.

The online acquisition of the quality characteristics mentioned above in the treatment process and process optimisation through control and closed-loop control thus belong to the important tasks of quality improvement.

For determination by means of measuring technologies of the above mentioned characteristics, "one-purpose-devices" are known in the prior art, such as optical systems for determining the flatness (flatness measurement systems), the strip widths (widths measurement systems) and the surface condition (surface inspection systems) and radiometric systems for determination of the strip thickness or the transverse profile of the strip thickness respectively. These systems operate independently of each other and are spatially spaced apart from each other, in order to exclude interference between eachother, which requires substantial building space.

For surface inspection optical systems are preferably used in the prior art.

These usually comprise the following components:

Illumination units to illuminate the strip surface, a camera unit for recording the strip surface without gap, a processing unit for processing the information of the camera image and an interface unit for process integration and display of the classification results.

In general, the following system types of surface inspection of strip are to be distinguished, namely systems with line cameras and systems with several CCD-matrix-cameras.

The illumination should preferably be designed in such a way, that the errors, that can occur in a specific production line, can be detected with best possible optical contrast. With matrix-cameras stroboscopic illuminations are used in general, which deliver the necessary light quantity in a short time interval. With line cameras permanent illumination units are used in general, whereby the motion blur is suppressed via the electronic camera shutter.

It has been tried to achieve a high homogeneity of the illumination, since image quality and detection performance are directly influenced by it. Each inhomogeneity in the illumination has to be adapted by boosting the image signal. This eventually leads to a reduction in the signal-noise-separation. With matrix-cameras the homogeneity of the illumination is advantageous, since the compensation via the image boosting in two directions is much more extensive than via a single line as with line-cameras. With all illuminations there are implementations in the visual part of the spectrum and in the IR- or UV-part. The light emission can be implemented diffuse or pointed through appropriate optical components.

The camera technology is preferably dimensioned in such a way, that the minimal error size under all speed conditions of the strip can still be resolved. The image recording takes place in relation to the strip length. In order to make full use of the dynamic-spectrum of the camera, the image brightness is preferably controlled automatically.

With the systems that have been in full operational use for a while, a distinct overbalance is registered with "line-cameras", since line-camera systems have been available on the market first and have at first been used on surfaces with low demands that were fairly simple to inspect. Many systems that use matrix-cameras have only been set up in the last two or three years and are not only for that reason still in the running-in phase or in performances checks. At present, it has to be said, that in principal there exists no significant difference in the performance between a matrix and a line camera system. Line camera systems are however less extensive in terms of setting up and operation.

The camera resolution is determined by the smallest error size to be classified and is restricted by the optical imaging laws. The minimal error size is preferably covered by at least 16 detected pixels, that is pixels detected as faulty by the system, in order to obtain a good classification in the downstream processing. For optimisation of the specific error imaging, the choice of direction of observation and the inclination of the cameras are of importance. Bright field and dark-field observations are predominant, recently side-field observations have also been used.

By combining the different illuminations and camera arrangements the optimal installation conditions for the respective application can be developed.

In the image processing unit the continuously recorded surface images are checked for information content. The characteristics of the "error images" can be compared with lodged error characteristics. In the case of respective concordance the automatic classification in one of the "pre-trained" error classes can be effected. The extraction and the comparison of the image characteristics demands large computing performance at present.

The presently available inspection systems compare the image points recorded with threshold levels. Image points identified as faulty are set, all others will not be set. From these "binary images" and with the brightness information lodged for each image point parameters for classification are obtained.

The interface-unit is usually designed application specific, in order to provide the surface inspection system with the important strip- and control-information in time. This is a standard task for the automation and database technology.

In the prior art, the described systems for the measuring of flatness and for surface inspection operate independently of eachother and are spaced apart from eachother, in order to exclude interference between eachother, which requires substantial building space.

BRIEF SUMMARY OF THE INVENTION

The object of the invention is to provide a system which allows an improved measurement and moreover can be designed space saving.

To this end a method and a device according to the independent claims is suggested.

Through the integration possibilities of the devices and the methods synergy effects are obtained that increase the measurement confidence.

The invention rests on the principle idea to bring together the flatness measurement and the surface inspection on the basis of image recognition, preferably with high resolution, fast line-cameras. The system can additionally be used for determining the strip-width or sheet-width respectively.

Dependent on the embodiment, the following advantages can arise:

The number of necessary components is reduced through "multiple-use", especially with regard to the illumination unit.

The necessary building space is noticeably reduced compared to single-use systems.

The inclusion of the results from the surface shape measurement into the width measurement increases the measurement confidence of the width measurement in the case of uneven strip shape.

The inclusion of the results from the surface shape measurement into the with measurement increses the measurement confidence of the width surface inspection allows for a distortion free error-representation, especially measurement in the case of uneven strip shape.

The inclusion of hte results from the surface shape measurement into the surface inspection allows for distortion free error-representation, especially with strip that do not lie in the pass-line due to flattering or that do not have a plane strip shape respectively. The image recording by means of line cameras is thus possible in sections where the strip is not tightened by additional devices, like a deflection roller.

An incorporation of the results of the surface-shape analysis ability reduces the pseudo-error portion of the surface inspection significantly.

The invention will now be described in more detail, by way of example, with reference to an embodiment illustrated in the drawings.

BRIEF DESCRIPTION OF THE DRAWINGS

The method according to the invention for optical measuring of the surface shape and for optical surface inspection can be use for any moving or stationary elongated body, preferably strip or sheet.

DETAILED DESCRIPTION OF THE INVENTION

Figure 5:
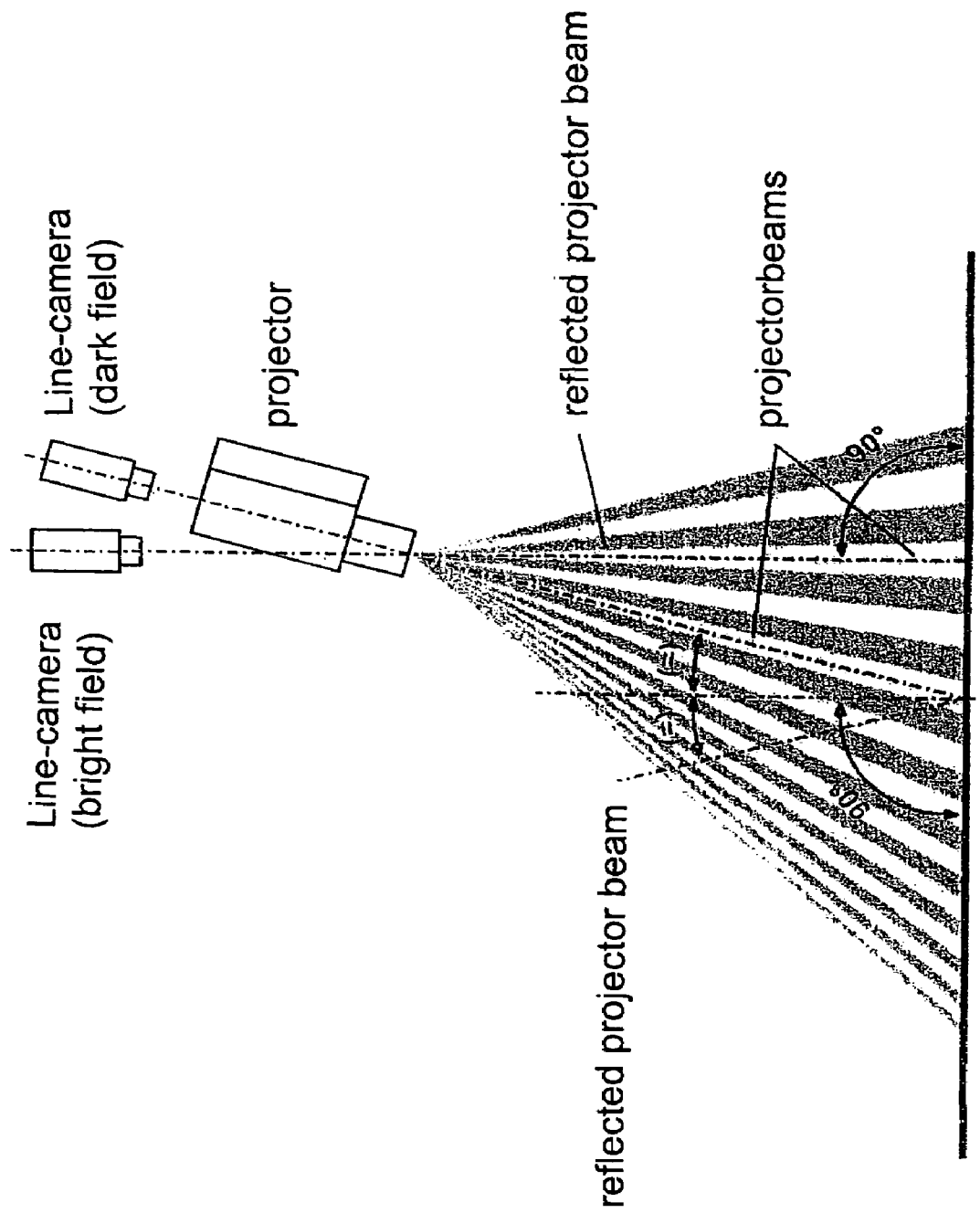
FIGS. 5 and 6 show the integration of the flatness measuring with the surface inspection in one device.
Figure 6:
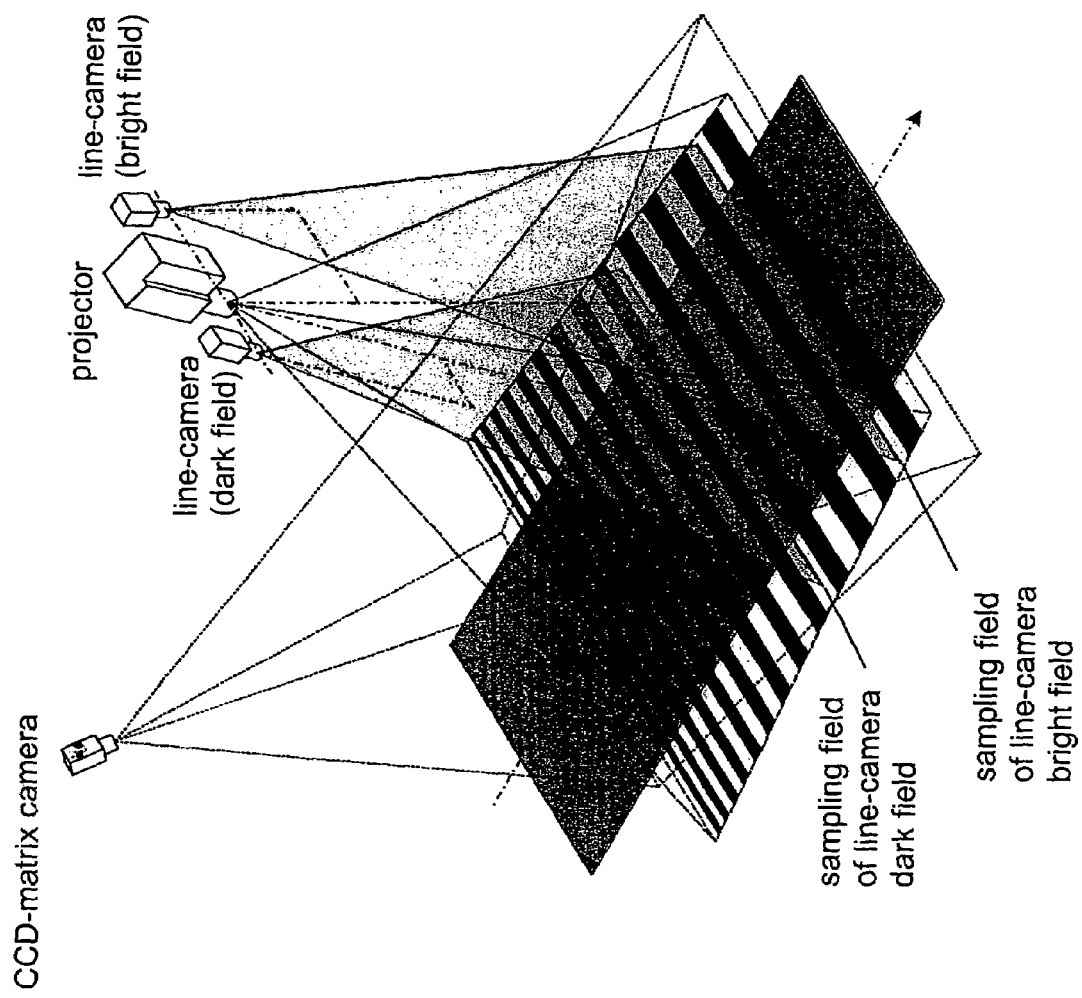

The device according to the invention preferably has the construction according to FIG. 5, with the line cameras positioned on the same axis as the projector.

Measurement lines 2 running transverse to the strip 1 are produced on the measurement or strip surface 4 using a protector 3.

The measuring arrangement is disposed in one case in the run-out from the finishing stands 6 and in the other case before the coiler 7, on an instrument case 13. The CCD camera 5 is located on the side of the instrument case nearer to the coiler 7, in a water-cooled housing. The projector 3 is located on the side of the instrument case remote from the coiler 7. To remove heat the housing is cooled with air. The cooling of the projector 3 and of the camera 5 is necessary to remove their intrinsic heat and the radiant heat from the strip 1, which is at about 1000 DEG C.

The camera 5 and the projector 3 are arranged in succession relative to the direction of travel of the strip and are aimed at a region of the strip located between them, on which the line pattern is produced and sampled. The projector used may, for example, be a xenon light source, which produces an easily readable line pattern even on a hot slab.

Unevenness on the strip surface 4 cause the measurement lines 2 to follow an irregular course or to depart from geometric straightness.

By means of a CCD camera 5 in the measurement lines 2, and consequently also the changes in their course caused by unevenness, are detected. After it has been detected the measurement image is compared by computer with a previously recorded reference pattern. The height differences and the parameters for the control of the finishing train are derived directly from the deviations.

A complete picture of the flatness of the strip or sheet 1 is thereby obtained as it moves along in the direction of the arrow. In principal the measurement can also take place with stationary rolling stock.

Figure 1:
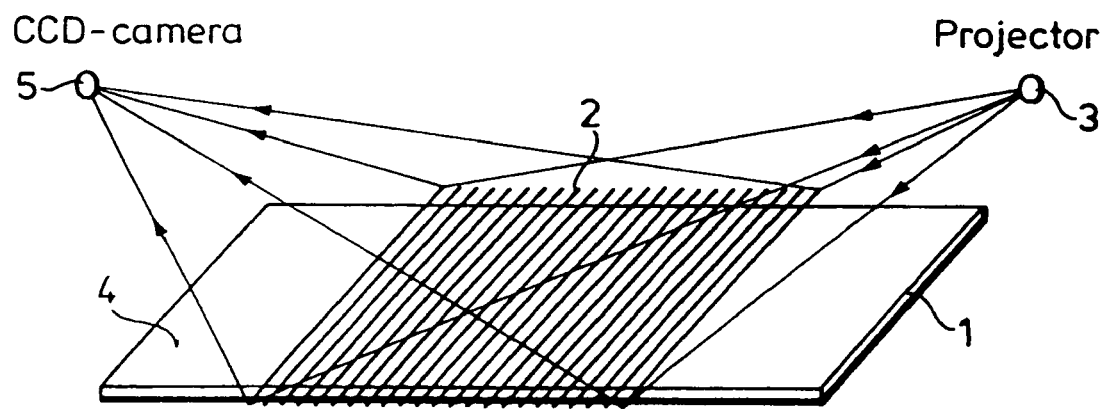
FIG. 1 shows the production and detection of the measurement lines on a length of strip.
Figure 2:
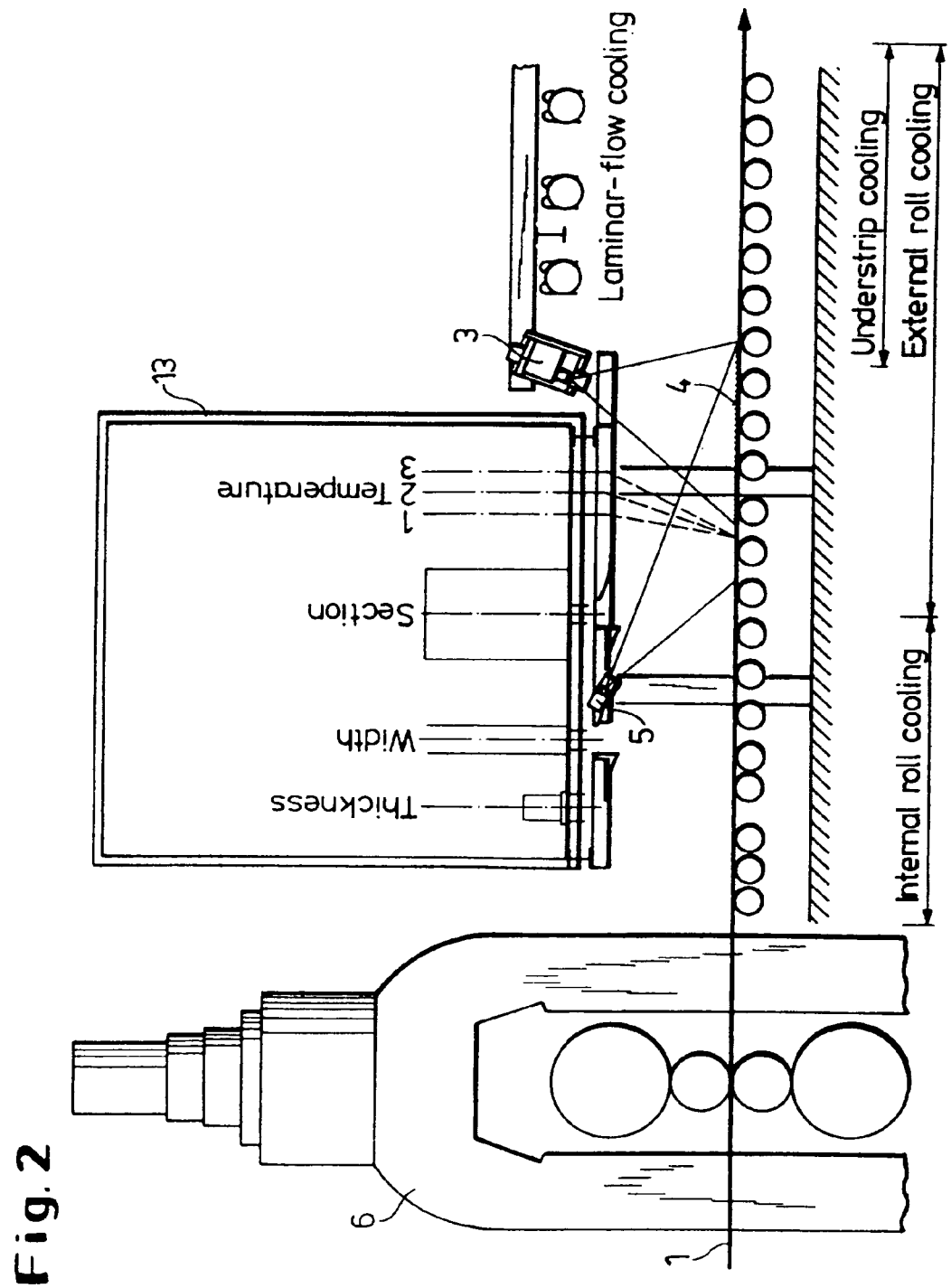
FIG. 2 shows a protector and a camera arranged after a finishing train.
Figure 3:
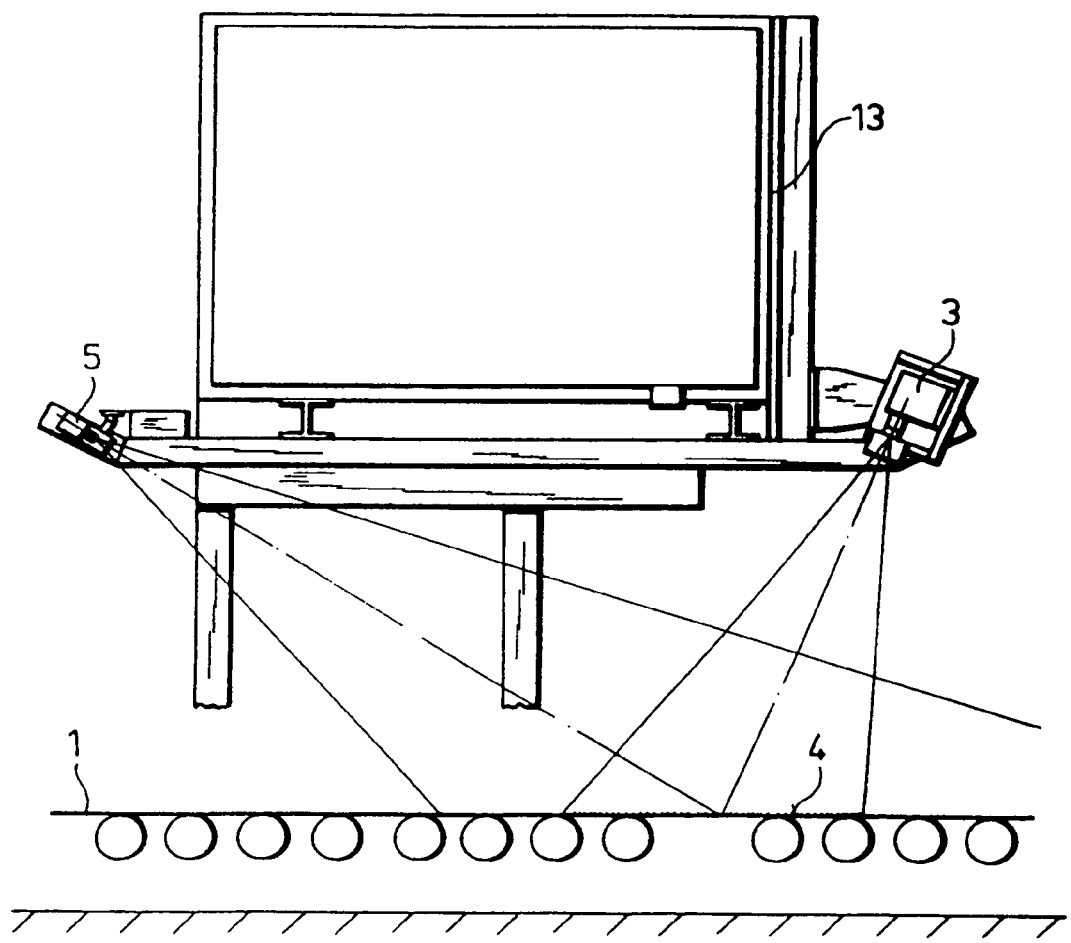
FIG. 3 shows the projector and the camera arranged before a coiler pit.
Figure 4:
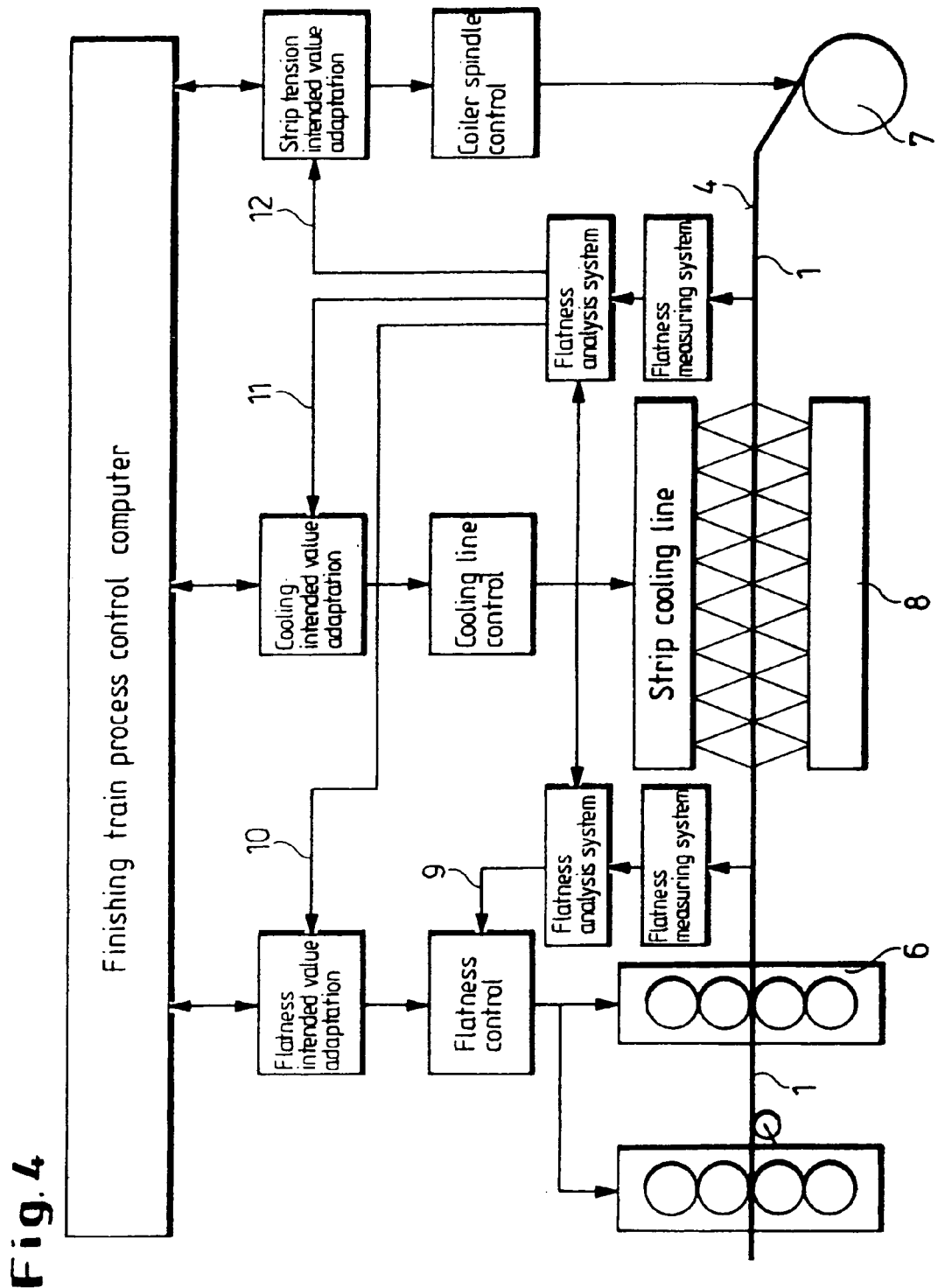
FIG. 4 is a block diagram of the flatness control system.

From the diagram of the flatness control system (FIG. 4) the design in accordance with the invention can be seen. The hot strip 1 passes through the finishing rolls 6 and the strip cooling line 8 to the coiler 7 in the coiler pit. In the runout from the finishing rolls 6 the flatness of the hot strip is detected, analysed and evaluated for control of the last stands of the finishing rolls (roll bending and tilting). This internal flatness-control loop 9 is supplemented by an external flatness-control loop 10. By a measurement of the strip flatness after the strip cooling line 8 before the coiler 7 the external flatness-control loop 10 is designed for adaptation of the intended value of the internal control loop.

Using the measured values detected after the strip cooling line a first secondary control loop 11 is also produced which permits the intended value for the cooling line 8 to be adapted and a second secondary control loop 12 which permits the intended value for the coiler tension 7 to be adapted.

The sampling of the strip surface for detection of imperfections (errors) is effected by additionally installed, high-resolution line cameras (FIG. 5), that allow for the detection of the surface across the complete strip width. Both line cameras are pointed to a ("bright") strip illuminated by the projector. The optical axis of the camera is orientated in the direction of the projection beams, in order to record the respective illuminated strip through the line camera even in the event of height changes of the strip surface. Due to the adapted arrangement of the two line cameras under consideration of the arrangement of the projector relative to the strip surface, it is achieved that one camera operates in the "bright field" and the second camera operates in the "dark field" (FIG. 5), which is necessary for the optimisation of the detection performance with surface imperfections of different characteristic. The images of both cameras are feed to an image processing unit for error identification.

For the geometrical deskewing of the image of the line cameras the height profiles along the measuring fields obtained by the flatness measuring system can be used.

Moreover in directly linking the information from the flatness measurement—especially the elongation profile transverse to the longitudinal direction—and the error images the identification of errors like transverse cracks and edge cracks for example, which can develop during the rolling process due to local exceedance of the breaking strength, can be improved, whereby an indication for the error cause can be deducted at the same time.

In addition to the surface inspection the image information of both line cameras can be used in combination to the results of the parallel flatness measurement for the height resolution quantitative determination of the strip edge position and the strip width. For this the height profiles along the measurement field determined with the flatness measurement system and the strip edge information detected by the line cameras are used for a geometric transformation.

The invention claimed is:

1. A method for optical measurement of surface shape and for optical surface inspection of moving strips in rolling and processing installations, the method comprising:
    continuously moving a strip through a rolling and processing installation;
    producing a pattern of lines on a part of the moving strip with a projector;
    recording an image of the pattern with a first camera;
    recording two further images of the part of the moving strip with a first line camera and a second line camera; and
    performing surface shape measurement and surface inspection on the basis of the recorded images.

2. The method according to claim 1, wherein surface shape measurement results are used in the surface inspection.

3. The method according to claim 1, wherein the first and second line cameras are situated on an axis with the projector.

4. The method according to claim 1, further including comparing the pattern with a reference pattern by computer after the image of the pattern is detected by the first camera.

5. The method according to claim 1, further including using measurement results to control a finishing train.

6. The method according to claim 1, wherein a xeon light is used as a projection light source.

7. A method for optical measurements, comprising:
    producing a pattern of lines on a part with a projector;
    recording an image of the pattern with a first camera;
    recording two further images of the part with a second camera and a third camera; and
    performing surface shape measurement on the basis of the recorded images;
    wherein the producing of a pattern of lines on a part includes producing the pattern of lines on a continuously moving strip moving through a rolling and processing installation.

8. The method according to claim 7, wherein the performing of surface shape measurement on the basis of the recorded images includes performing surface inspection.

9. The method according to claim 7, wherein the recording of two further images of the part with a second camera and a third camera includes recording the two further images with the second and third line cameras situated on an axis with the projector.

10. The method according to claim 7, further including comparing the pattern with a reference pattern by computer after the image of the pattern is detected by the first camera.

11. The method according to claim 7, further including using measurement results to control a finishing train.

12. The method according to claim 7, wherein the producing of a pattern of lines on a part with a projector includes producing the pattern using a xenon light as a projection light source.

13. A method for optical measurements, comprising:
    producing a pattern of lines on a part with a projector;
    recording an image of the pattern with a first camera;
    recording images of the part with a second camera and a third camera, wherein an optical axis of one of the second camera or third camera is normal to the part; and
    performing surface shape measurement on the basis of the recorded images:
    wherein the producing of a pattern of lines on a part includes producing the pattern of lines on a continuously moving strip moving through a rolling and processing installation.

14. The method according to claim 13, wherein the recording of images of the part with a second camera and a third camera includes recording with an optical axis of the other of the second camera or the third camera forming an angle with the optical axis of the one of the second camera or third camera.

15. The method according to claim 13, wherein the recording of images of the part with a second camera and a third camera includes recording images of the part with the second and third cameras situated on an axis with the projector.

16. The method according to claim 13, wherein the performing of surface shape measurement on the basis of the recorded images includes performing surface inspection.

17. The method according to claim 16, wherein surface shape measurement results are used in the surface inspection.

18. The method according to claim 13, further including comparing the pattern with a reference pattern by computer after the image of the pattern is detected by the first camera.

* * * * *